United States Patent
Yan et al.

(10) Patent No.: US 11,243,216 B2
(45) Date of Patent: *Feb. 8, 2022

(54) MOBILE DEVICE HAVING HEMOGLOBIN DETECTING FUNCTION AND HEMOGLOBIN DETECTING METHOD

(71) Applicant: REDEYE INC., Hsinchu (TW)

(72) Inventors: Shuo-Ting Yan, Hsinchu (TW); Kuan-Wei Su, Hsinchu (TW); I-Hua Wang, Hsinchu (TW); Chen-Chung Chang, Hsinchu (TW)

(73) Assignee: Taiwan Redeye Biomedical Inc., Hsinchu (TW)

( * ) Notice: Subject to any disclaimer, the term of this patent is extended or adjusted under 35 U.S.C. 154(b) by 363 days.

This patent is subject to a terminal disclaimer.

(21) Appl. No.: 16/406,189

(22) Filed: May 8, 2019

(65) Prior Publication Data

US 2020/0355702 A1 Nov. 12, 2020

(51) Int. Cl.
*G01N 33/72* (2006.01)
*G01N 21/31* (2006.01)

(52) U.S. Cl.
CPC .......... *G01N 33/726* (2013.01); *G01N 21/31* (2013.01); *G01N 33/721* (2013.01)

(58) Field of Classification Search
CPC .......... G01N 2021/3148; G01N 21/31; G01N 2201/0221; G01N 33/721; G01N 33/726; G01N 33/49
USPC ....... 436/63, 66, 164, 165; 422/82.05, 82.09
See application file for complete search history.

(56) References Cited

U.S. PATENT DOCUMENTS

| | | | | |
|---|---|---|---|---|
| 8,483,789 | B2* | 7/2013 | Higgins | A61B 5/0075 600/328 |
| 9,185,200 | B2* | 11/2015 | Cunningham | G01N 21/31 |
| 10,145,787 | B2* | 12/2018 | Yan | G01N 21/31 |
| 10,746,652 | B1* | 8/2020 | Yan | G01N 33/4833 |
| 10,761,015 | B1* | 9/2020 | Yan | G01N 33/721 |
| 10,823,665 | B2* | 11/2020 | Yan | G01J 3/42 |
| 10,877,022 | B1* | 12/2020 | Yan | G01N 21/01 |
| 10,883,927 | B2* | 1/2021 | Yan | G01N 21/31 |
| 2006/0222567 | A1* | 10/2006 | Kloepfer | G01N 33/558 422/68.1 |
| 2014/0038222 | A1* | 2/2014 | Alt | G01N 21/648 435/29 |
| 2017/0292908 | A1* | 10/2017 | Wilk | G01J 3/0289 |

(Continued)

*Primary Examiner* — Maureen Wallenhorst
(74) *Attorney, Agent, or Firm* — Rosenberg, Klein & Lee

(57) ABSTRACT

A hemoglobin detecting method is executed by a mobile device having a hemoglobin detecting function. The mobile device includes a processor unit, a first light source that generates a first light beam, and a light detecting module that receives a second light beam that is generated when the first light beam travels through an analyte solution and is reflected. The light detecting module generates first to fourth intensity signals according to the second light beam, and the processor unit determines whether the absorption spectrum of the analyte solution matches a target spectrum. If the absorption spectrum of the analyte solution matches the target spectrum, the processor unit generates positive result information; otherwise, the processor unit generates negative result information. The mobile device provides a fast and accurate way to detect blood in a stool solution, which does not require collecting samples of stool or applying any chemical.

19 Claims, 16 Drawing Sheets

(56) References Cited

U.S. PATENT DOCUMENTS

| | | | |
|---|---|---|---|
| 2017/0303901 A1* | 10/2017 | Sekine | G01N 33/4833 |
| 2018/0085098 A1* | 3/2018 | Attar | G01N 33/493 |
| 2019/0008392 A1* | 1/2019 | Wang | A61B 5/08 |

* cited by examiner

MOBILE DEVICE HAVING HEMOGLOBIN DETECTING FUNCTION AND HEMOGLOBIN DETECTING METHOD

BACKGROUND OF THE INVENTION

1. Field of the Invention

The present invention relates to a mobile device and a detecting method, particularly a mobile device having a hemoglobin detecting function and a hemoglobin detecting method executed by the mobile device.

2. Description of the Related Art

Hemoglobin exists in the blood of humans and most animals. When tissue inflammation, cancer tissue growth, or ulcers occur in internal organs, blood might leak from the damaged tissue, causing hemoglobin to appear in secretion such as stool, urine, saliva, or snivel. Therefore, detecting the hemoglobin in such secretion can be a crucial index for some specific lesions or diseases. For instance, stool occult blood test is an index for colorectal cancer, urine occult blood test is an index for bladder cancer, and sputum occult blood test is an index for bronchitis or lung cancer. Among all cancers, colorectal cancer is one of the most commonly diagnosed cancers around the world. In the USA, 8% of the total cancer cases is colorectal cancer, which is ranked the $4^{th}$ among all cancers with a mortality rate ranked the second. China has 18.6% of the global colorectal cancer cases, with 20.1% of the mortalities in the world.

As stated above, one of the most commonly used index for colorectal cancer is the occult blood test. In other words, if blood or hemoglobin appears in the stool, it is likely that colorectal cancer or early stage symptom of such is appearing. Nowadays, the most common solution for stool occult blood test is immunochemical fecal occult blood test (i-FOBT). In the procedure of i-FOBT, the subject is required to collect a sample of the fecal secretion, and send the sample back to the hospital by delivery or in person, so that the medical technologist can perform the occult blood test on the sample. However, such process needs long waiting time and leads to inconvenience, so normally the general public may only go through related physical examinations once a year or two. The inspection cycle is too long to discover the symptom as soon as it shows. On the other hand, blood tissue is not uniformly distributed in the stool, and the sample is only a small portion of the stool that may not include the part that contains blood, leading to a pseudo-negative result, which means the result of the occult blood test is negative, but a tumor or a polyp is already growing inside the intestine and causes bleeding. On the other hand, a tumor or a polyp may be bleeding intermittently instead of constantly. If the lesion did not bleed before or on the day the fecal sample is taken, the result of the occult blood test might also be pseudo-negative and leads to misdiagnosis.

In one of the related arts of remotely detecting stool or urine occult blood, a fluorescent agent or oxidant must be added into the toilet bowl before irradiating the solution in the toilet bowl with excitation light, and then detecting the photoluminescence from the solution to determine whether the secretion contains hemoglobin or blood. The operator must prepare the chemicals, leading to inconvenience.

In some other related art of remotely detecting stool or urine occult blood which also utilize photoluminescence detection method, analyte such as stool or urine must be added into a reaction solution. The reaction solution includes multiple strong reducing agents that may cause burn when in contact with the skin.

In another related art, the operator of an occult blood test must collect the sample of the stool, and put it in the dilution liquid. After the testing process, the container must be cleaned with extra cleaning processes.

To sum up, among the related arts of secretion occult blood test, some require collected sample of stool or urine, while some require the use of additional chemicals for reaction such as fluorescent agent or reducing agent. Those procedures are complex and inconvenient, or even lead to potential danger, which may not be done frequently and not suitable for users to conduct at home.

SUMMARY OF THE INVENTION

An objective of the present invention is to provide a mobile device having a hemoglobin detecting function.

The mobile device having the hemoglobin detecting function includes a processor unit, a first light source, and a light detecting module. The first light source generates a first light beam, which is used to pass through an analyte solution and be reflected to form a second light beam. The second light beam includes a first wavelength light, a second wavelength light, a third wavelength light, and a fourth wavelength light. The light detecting module receives the second light beam and generates a light intensity information. The light intensity information includes a first intensity signal relating to the first wavelength light, a second intensity signal relating to the second wavelength light, a third intensity signal relating to the third wavelength light, and a fourth intensity signal relating to the fourth wavelength light. A wavelength of the first wavelength light is smaller than a wavelength of the second wavelength light, the wavelength of the second wavelength light is smaller than a wavelength of the third wavelength light, and the wavelength of the third wavelength light is smaller than a wavelength of the fourth wavelength light.

Furthermore, the processor unit receives the light intensity information from the light detecting module, and determines whether the absorption spectrum of the analyte solution matches a target spectrum. The spectrum of the analyte solution matches the target spectrum if the second intensity signal, the third intensity signal and the fourth intensity signal are larger than the first intensity signal, and the second intensity signal and the fourth intensity signal are larger than the third intensity signal.

When the absorption spectrum of the analyte solution matches the target spectrum, the processor unit generates a positive result information; when the absorption spectrum of the analyte solution does not match the target spectrum, the processor unit generates a negative result information.

The mobile device having the hemoglobin detecting function provides users with a convenient tool to detect occult blood in stool. The mobile device can be a smart phone, a tablet computer, or a PDA, etc. The first light source can be the LED light or flash light module for assisting photo shooting, which is mounted on the back of the mobile device and beside the camera. When a user turns on the first light source and points the first light source to a container containing the analyte solution, the first light beam passes through the analyte solution, and the first light beam is reflected by a reflection surface of the container to form the second light beam.

The analyte solution is a liquid that includes human fecal extraction, for instance, the liquid solution in a toilet bowl that contains stool. When stool carrying blood tissue falls into the water in the toilet bowl, the blood in the stool will dissolve into the water around it. That is, if occult blood exists in the stool, the blood will also exist in the water in the toilet bowl, which is the analyte solution of the present invention. Furthermore, when the first light beam passes through the analyte solution, the first light beam will be partially absorbed by the analyte solution, and the second light beam, the reflected light beam of the first light beam, will contain information of the absorption spectrum of the analyte solution.

When the processor unit receives the light intensity information generated by the light detecting module, the processor unit determines whether the absorption spectrum of the analyte solution matches the target spectrum. The target spectrum is the absorption spectrum of a blood solution. If the processor unit determines that the absorption spectrum of the analyte solution matches the target spectrum, it is confirmed that the analyte solution contains blood tissues, which indicates that the stool in the toilet bowl contains occult blood. Therefore the processor unit generates a positive result information. If the processor unit determines that the absorption spectrum of the analyte solution does not match the target spectrum, it is confirmed that the analyte solution does not contain blood tissue, which indicates that the stool in the toilet bowl does not contain occult blood. Therefore the processor unit generates a negative result information.

Since the mobile device of the present invention analyzes the absorption spectrum of the liquid containing the stool rather than testing the stool itself, it avoids the possibility of a pseudo-negative result caused by the collected sample not containing the part with blood, thus improving the reliability of the test results. In the process of detecting occult blood in stool using the mobile device, there is no sample collecting, no solution stirring, and no long waiting time for the result, thus enhancing the convenience of the whole process. On the other hand, the device directly performs analyzation on the absorption spectrum of the solution itself by sending the first light beam and receiving the second light beam. So there is no need for adding any chemical agent such as fluorescent agent, reaction agent, or reductant, thereby eliminating the risks of user exposure to chemicals or environmental pollution.

In conclusion, the present invention provides a fast, easy and safe way to perform a stool occult blood test. Any ordinary user can perform self-examination for stool occult blood at home and obtain a result instantly, doing health management efficiently and independently.

Other objectives, advantages and novel features of the invention will become more apparent from the following detailed description when taken in conjunction with the accompanying drawings.

DETAILED DESCRIPTION OF THE INVENTION

Figure 1:
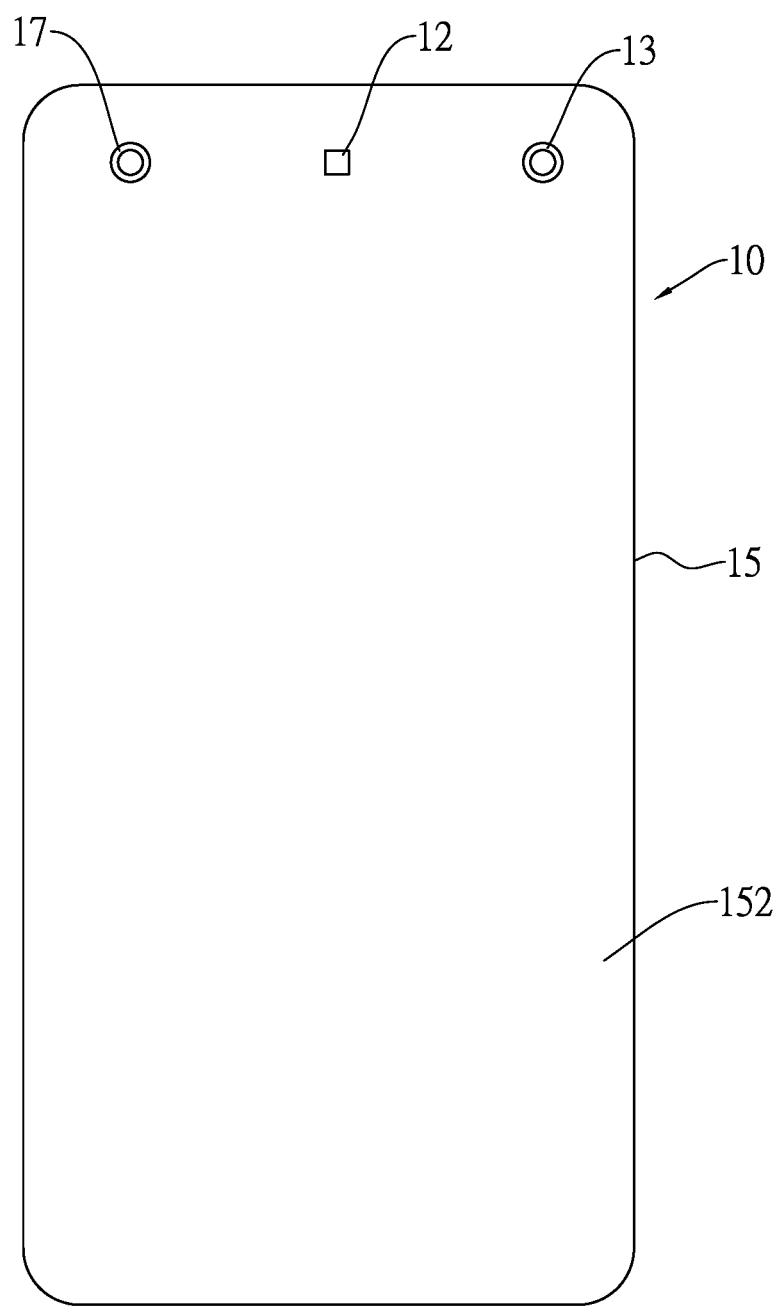
FIG. 1 is a schematic view of the back side of a mobile device having a hemoglobin detecting function of the present invention.
Figure 2:
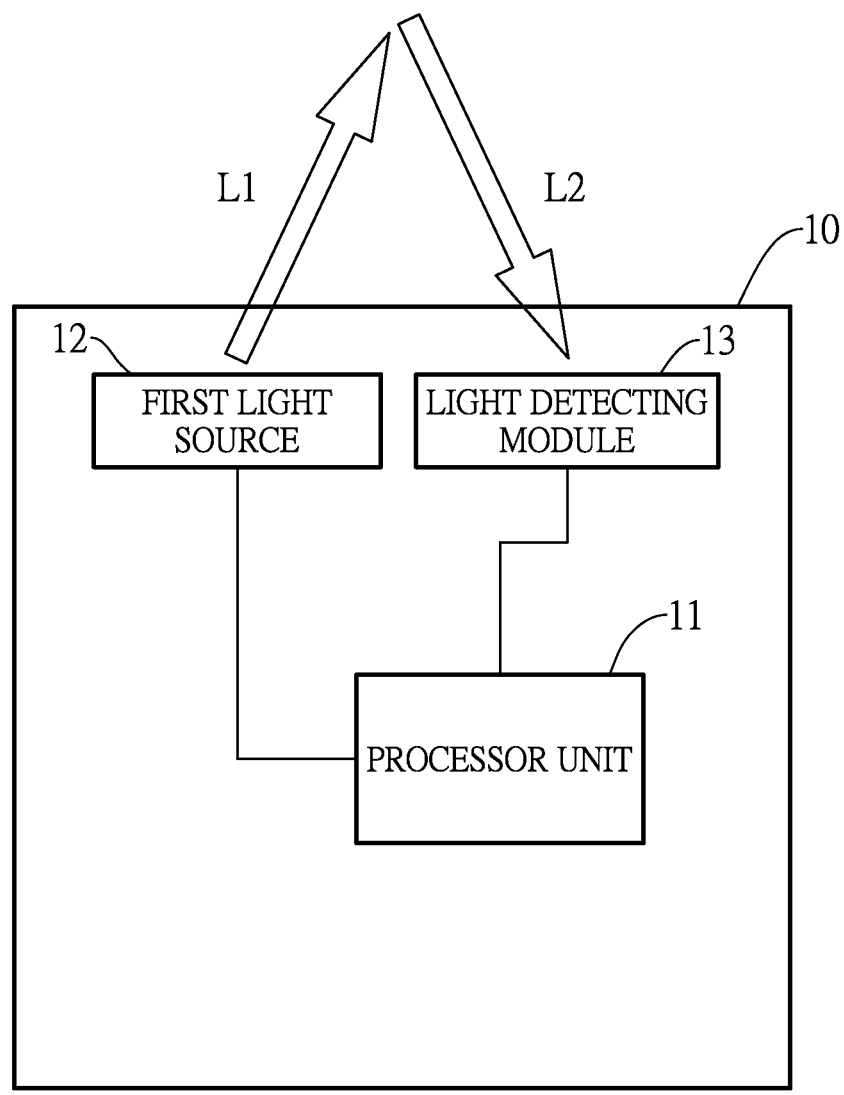
FIG. 2 is a block diagram of the mobile device having the hemoglobin detecting function of the present invention.

With reference to FIG. 1 and FIG. 2, a mobile device 10 having a hemoglobin detecting function includes a processor unit 11, a first light source 12, and a light detecting module 13. The light detecting module 13 is electrically connected to the processor unit 11. The first light source 12 generates a first light beam L1, which is directed to an analyte solution. The first light beam L1 passes through the analyte solution and is reflected to form a second light beam L2. The second light beam L2 includes a first wavelength light, a second wavelength light, a third wavelength light, and a fourth wavelength light. The light detecting module 13 receives the second light beam L2, and generates a light intensity information. The light intensity information includes a first intensity signal S1 relating to the first wavelength light, a second intensity signal S2 relating to the second wavelength light, a third intensity signal S3 relating to the third wavelength light, and a fourth intensity signal S4 relating to the fourth wavelength light. A wavelength of the first wavelength light is smaller than a wavelength of the second wavelength light, the wavelength of the second wavelength light is smaller than a wavelength of the third wavelength light, and the wavelength of the third wavelength light is smaller than a wavelength of the fourth wavelength light.

Furthermore, the processor unit 11 receives the light intensity information from the light detecting module 13, and determines whether the absorption spectrum of the analyte solution matches a target spectrum. The spectrum of the analyte solution matches the target spectrum if:

the second intensity signal S2, the third intensity signal S3 and the fourth intensity signal S4 are larger than the first intensity signal S1; and the second intensity signal S2 and the fourth intensity signal S4 are larger than the third intensity signal S3.

When the absorption spectrum of the analyte solution matches the target spectrum, the processor unit 11 generates a positive result information; when the absorption spectrum of the analyte solution does not match the target spectrum, the processor unit 11 generates a negative result information.

Figure 3:
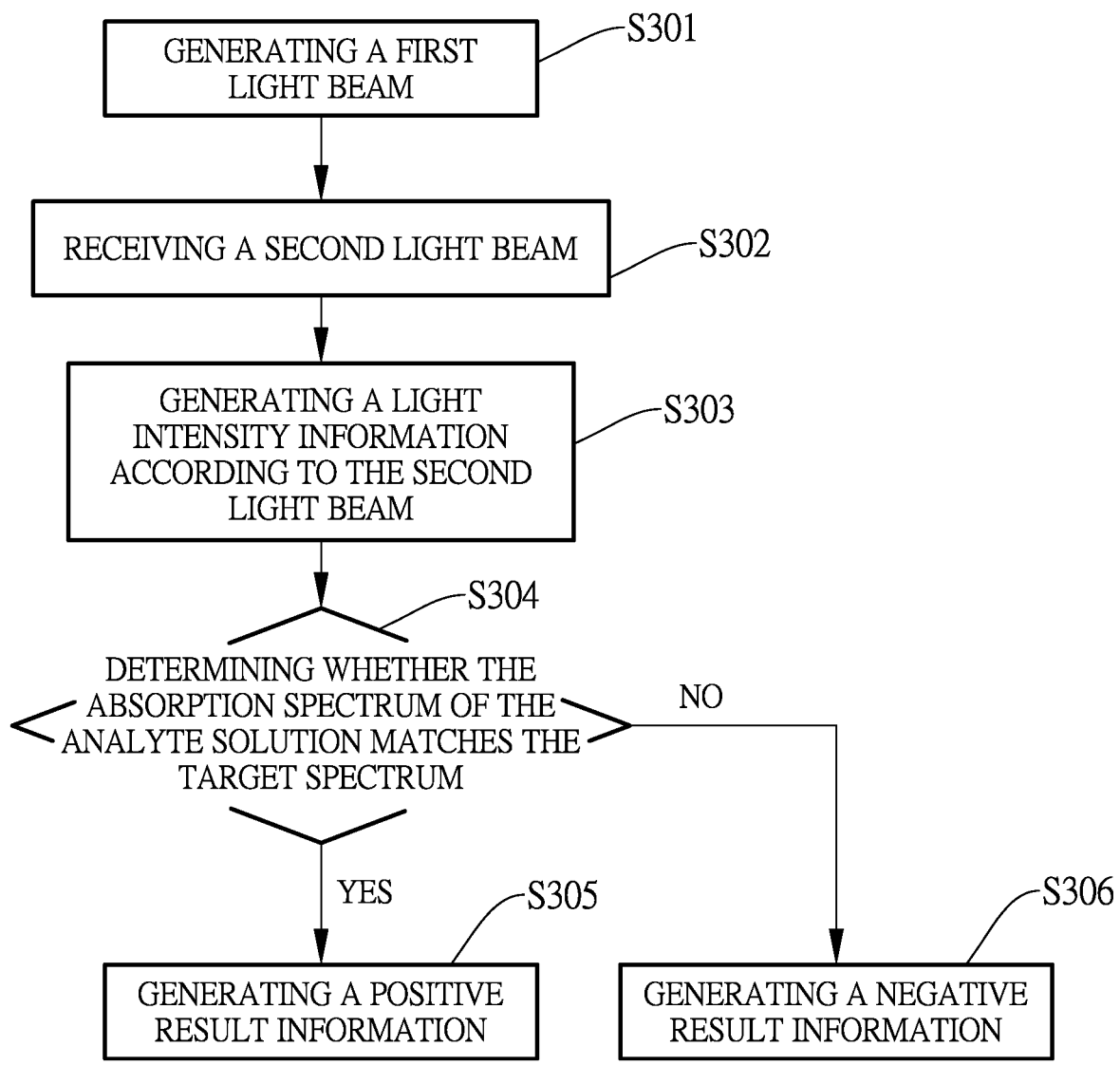
FIG. 3 is a flow diagram of a hemoglobin detecting method of the present invention.

With reference to FIG. 3, the present invention provides a hemoglobin detecting method, including the following steps:

generating a first light beam L1 (S301);

receiving a second light beam L2, which is formed by the first light beam L1 passing through the analyte solution and being reflected (S302)

generating a light intensity information (S303); wherein the light intensity information includes a first intensity signal S1 relating to the first wavelength light, a second intensity signal S2 relating to the second wavelength light, a third intensity signal S3 relating to the third wavelength light, and a fourth intensity signal S4 relating to the fourth wavelength light;

determining whether the absorption spectrum of the analyte solution matches the target spectrum according to the light intensity information (S304);

when the absorption spectrum of the analyte solution matches the target spectrum, generating a positive result information (S305);

when the absorption spectrum of the analyte solution does not match the target spectrum, generating a negative result information (S306); wherein the spectrum of the analyte solution matches the target spectrum if:

the second intensity signal S2, the third intensity signal S3 and the fourth intensity signal S4 are larger than the first intensity signal S1; and the second intensity signal S2 and the fourth intensity signal S4 are larger than the third intensity signal S3.

In an embodiment of the present invention, the wavelength of the first wavelength light is 500 nm, the wavelength of the second wavelength light is 541 nm, the wavelength of the third wavelength light is 550 nm, and the wavelength of the fourth wavelength light is 577 nm.

Figure 4:
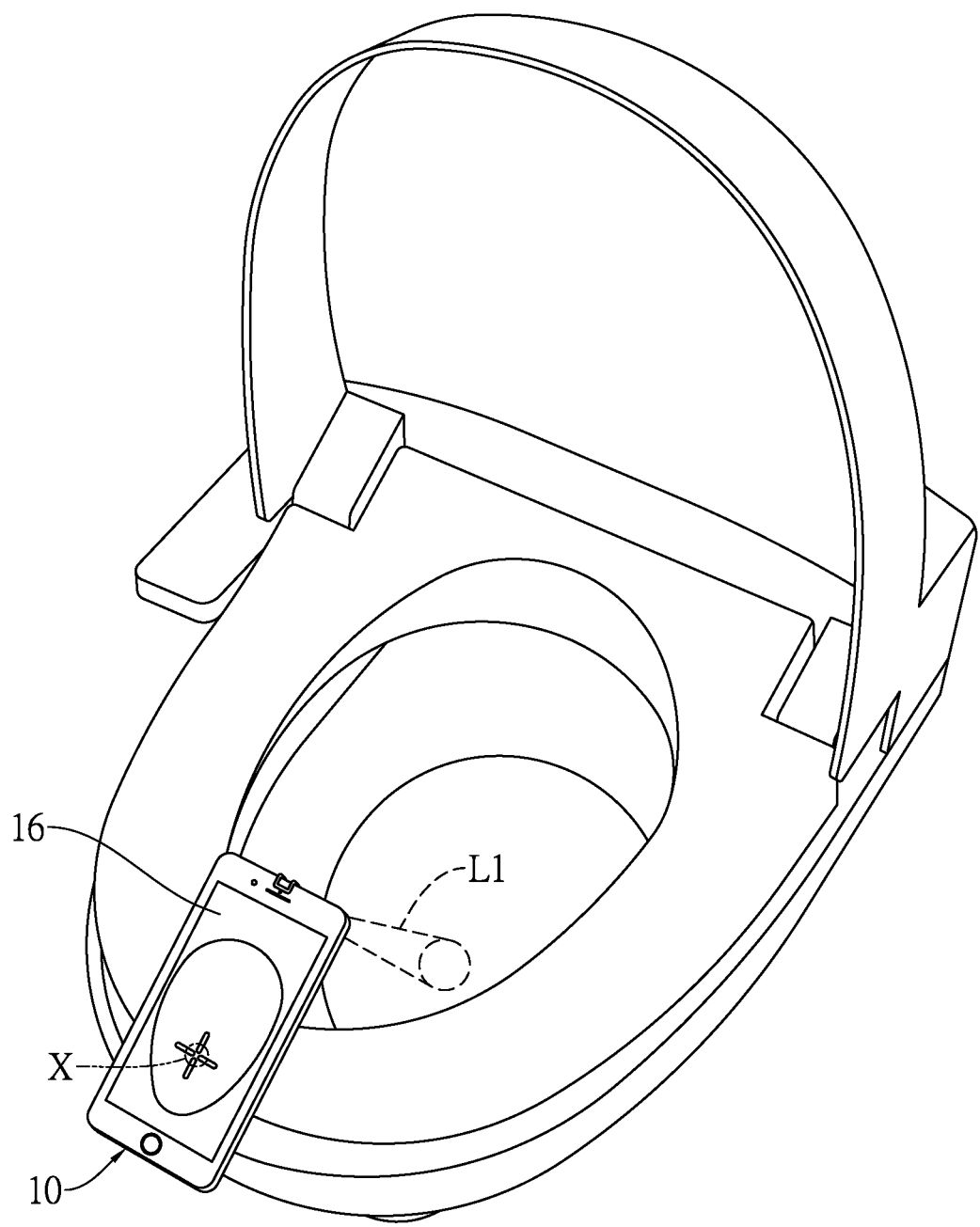
FIG. 4 is an operational schematic view of the mobile device having the hemoglobin detecting function of the present invention.

With reference to FIG. 4, a user may hold the mobile device 10 toward the analyte solution in a toilet bowl. The user may further point the first light beam L1 to the analyte solution, so that the light detecting module 13 receives the second light beam L2, which has passed through the analyte solution and been reflected by the inside surface of the toilet bowl. Therefore, the second light beam L2 will contain the absorption of the analyte solution. Preferably, a user should direct the first light beam L1 to a relatively shallow point in the toilet bowl.

Figure 5:
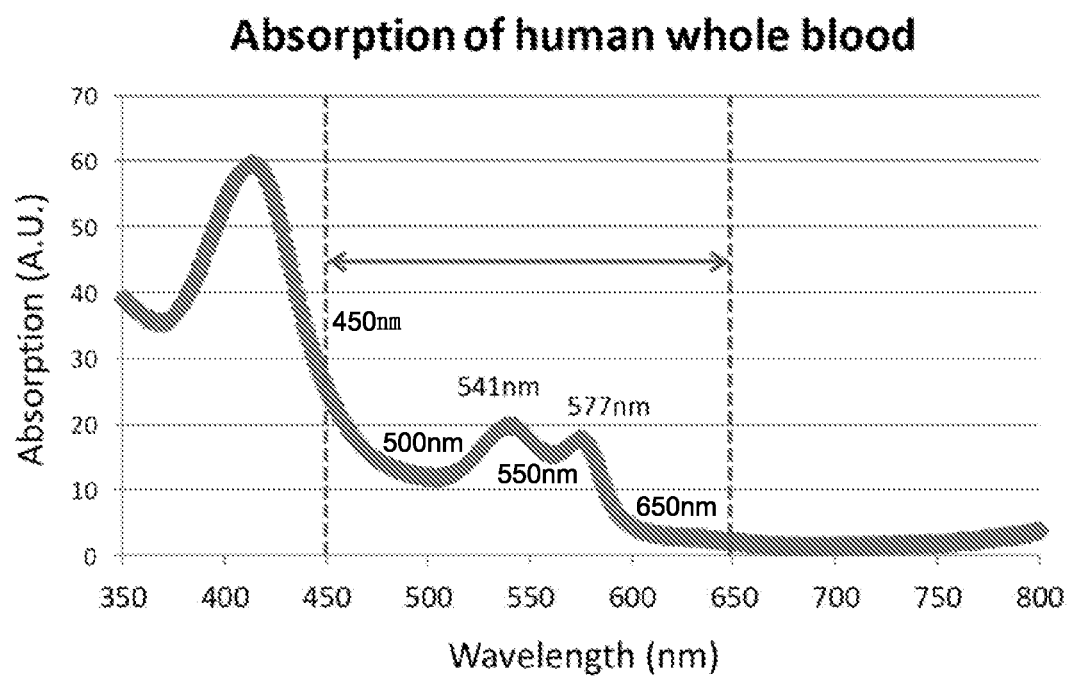
FIG. 5 is an absorption spectrum graph of a target spectrum of the mobile device having the hemoglobin detecting function of the present invention.

Please to FIG. 5, which is an absorption spectrum of a blood solution and also the target spectrum of the present invention. A LED light source may generate a light beam that covers most of the visible light frequency bandwidths, which include wavelengths ranging from 450 nm to 650 nm. Therefore, in the present embodiment, the determination is made according to the bandwidth of the first light beam L1 and the feature of the target spectrum. The light detecting module 13 detects the intensity signals corresponding to the wavelengths of 500 nm, 541 nm, 550 nm and 577 nm, which are feature points in the target spectrum, so that the processor unit 11 can determine whether the absorption spectrum of the analyte solution matches the target spectrum.

According to the target spectrum shown in FIG. 5, it is apparent that within the absorption spectrum of a blood solution, the intensity of light with wavelengths of 541 nm and 577 nm is higher than the intensity of light with wavelength of 550 nm, while the intensity of light with wavelengths of 541 nm, 550 nm, and 577 nm is higher than the intensity of light with wavelength of 500 nm. Therefore, the processor unit 11 determines whether the absorption spectrum of the analyte solution matches the target spectrum according to the first, the second, the third, and the fourth intensity signals S1-S4 that correspond to those feature points.

Figure 6:
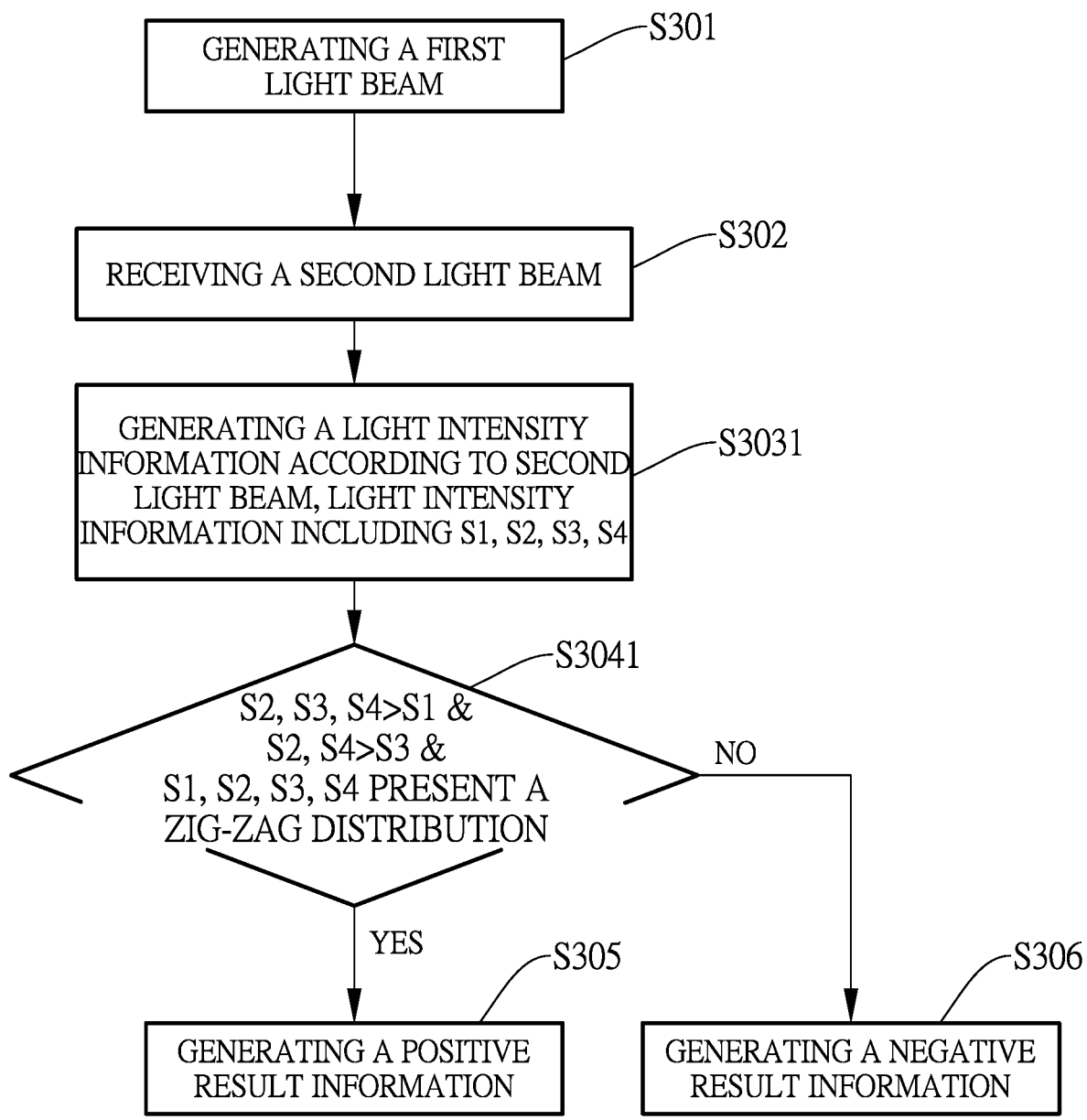
FIG. 6 is a flow chart of a first embodiment of the hemoglobin detecting method of the present invention.

With reference to FIG. 6, in a first embodiment of the present invention, when the processor unit 11 determines whether the absorption spectrum of the analyte solution matches the target spectrum, the processor unit 11 further determines if the first intensity signal S1, the second intensity signal S2, the third intensity signal S3, and the fourth intensity signal S4 present a zig-zag distribution (S3041). Furthermore, the processor unit 11 determines the absorption spectrum of the analyte solution matches the target spectrum (S305) only if:

the second intensity signal S2, the third intensity signal S3 and the fourth intensity signal S4 are larger than the first intensity signal S1;

the second intensity signal S2 and the fourth intensity signal S4 are larger than the third intensity signal S3; and the first intensity signal S1, the second intensity signal S2, the third intensity signal S3 and the fourth intensity signal S4 present a zig-zag distribution.

In the first embodiment, the processor unit further determines whether the first intensity signal S1, the second intensity signal S2, the third intensity signal S3 and the fourth intensity signal S4 should present a zig-zag distribution, which is another feature of the target spectrum. With such further condition, the accuracy of the detection is improved.

Figure 7:
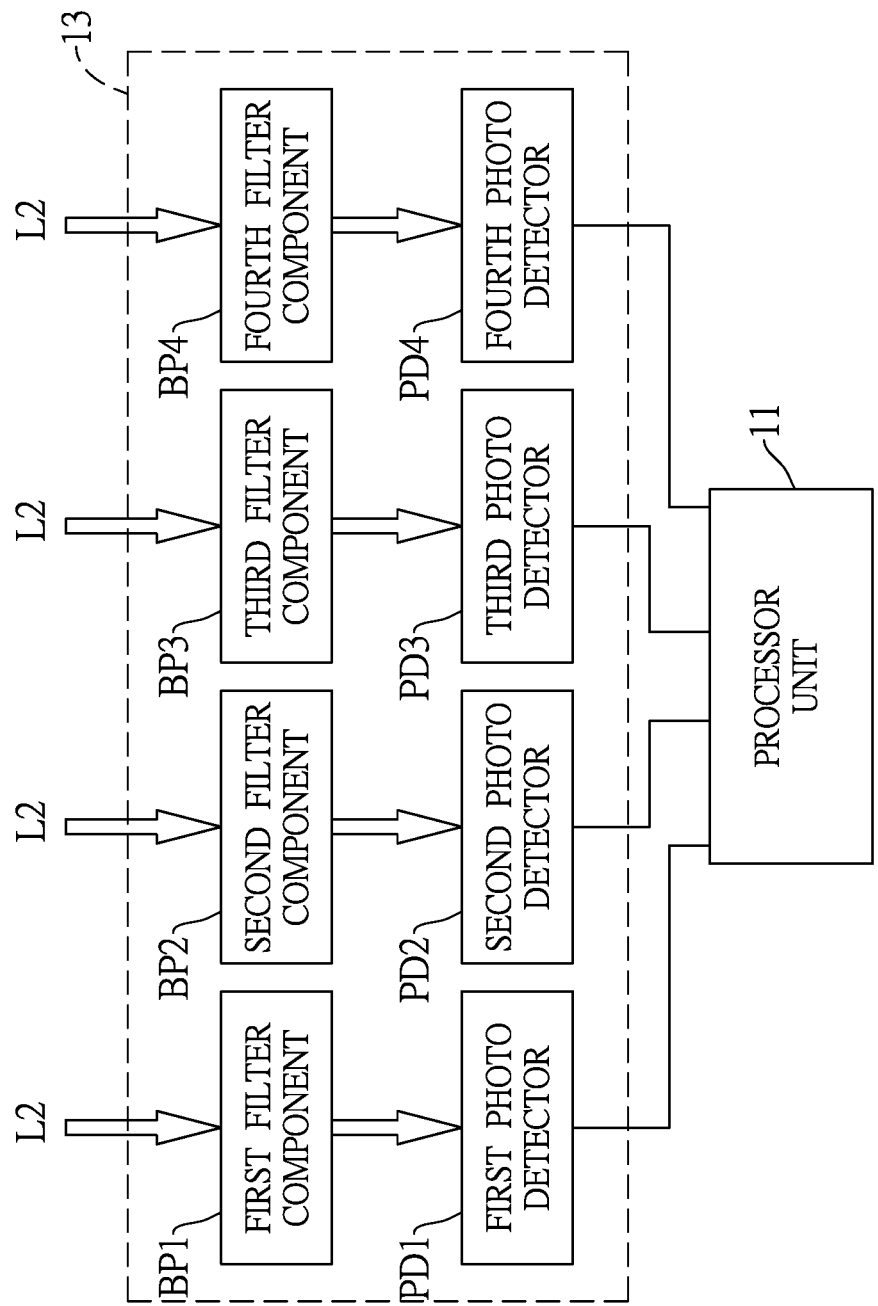
FIG. 7 is a block diagram of the light detecting module of the mobile device having the hemoglobin detecting function of the present invention.

With reference to FIG. 7, in the present embodiment, the light detecting module 13 includes a first filter component, a second filter component, a third filter component, and a fourth filter component. The light detecting module 13 further includes a first photo detector PD1, a second photo detector PD2, a third photo detector PD3, and a fourth photo detector PD4. The first photo detector PD1 receives the first wavelength light through the first filter component; the second photo detector PD2 receives the second wavelength light through the second filter component; the third photo detector PD3r receives the third wavelength light through the third filter component; the fourth photo detector PD4 receives the fourth wavelength light through the fourth filter component. In the present embodiment, the first filter component BP1 is a 500 nm wavelength bandpass filter, the second filter component BP2 is a 541 nm wavelength bandpass filter, the third filter component BP3 is a 550 nm wavelength bandpass filter, and the fourth filter component BP4 is a 571 nm wavelength bandpass filter. Therefore, when the second light beam L2 arrives at the light detecting module 13, the first photo detector PD1, the second photo detector PD2, the third photo detector PD3, and the fourth photo detector PD4 receive the first wavelength light, the second wavelength light, the third wavelength light, and the fourth wavelength light, respectively, through the first filter component, the second filter component, the third filter component, and the fourth filter component, respectively, thus generate the first intensity signal S1, the second intensity signal S2, the third intensity signal S3, and the fourth intensity signal S4, respectively.

In a second embodiment of the present invention, the light intensity information generated by the light detecting module 13 further includes a fifth intensity signal S5 relating to a fifth wavelength light and a sixth intensity signal S6 relating to a sixth wavelength light. A wavelength of the fifth wavelength light is shorter than a wavelength of the first wavelength light, and the wavelength of the sixth wavelength light is longer than the wavelength of the fourth wavelength light.

In the present embodiment, when the processor unit 11 determines whether the absorption spectrum of the analyte solution matches the target spectrum according to the light intensity information, the processor unit 11 further determines whether the fifth intensity signal S5 is larger than the first intensity signal S1. Furthermore, the processor unit 11 determines that the spectrum of the analyte solution matches the target spectrum when the light intensity information also meets the following condition: the fifth intensity signal S5, the first intensity signal S1, the second intensity signal S2, the third intensity signal S3, and the fourth intensity signal S4 are larger than the sixth intensity signal S6 (S3042).

Figure 8:
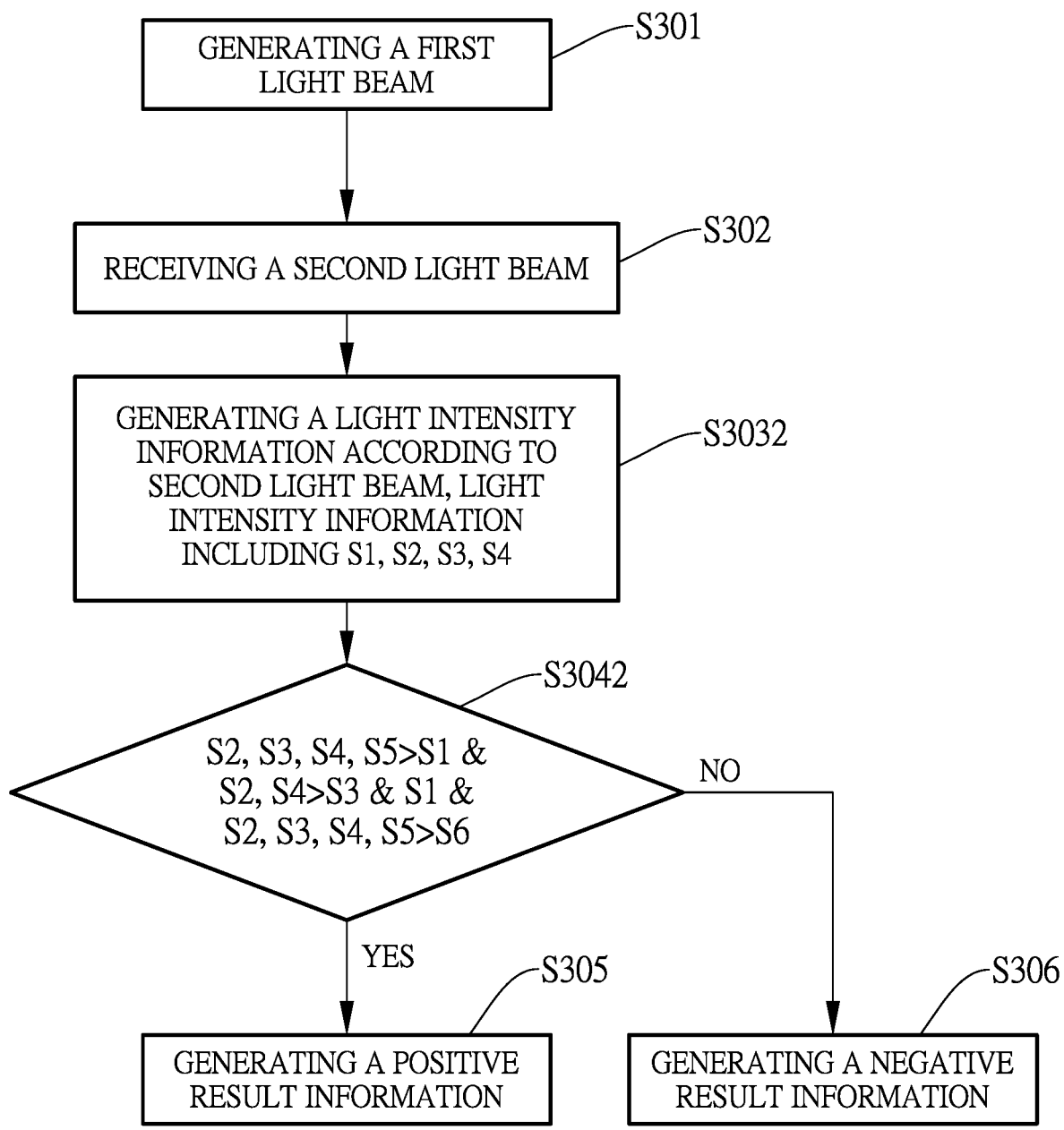
FIG. 8 is a flow chart of a second embodiment of the hemoglobin detecting method of the present invention.

With reference to FIG. 8, to be more specific, in the step of determining whether the absorption spectrum of the analyte solution matches the target spectrum according to the light intensity information (S304), the absorption spectrum of the analyte solution matches the target spectrum if:
- the second intensity signal S2, the third intensity signal S3, the fourth intensity signal S4 and the fifth intensity signal S5 are larger than the first intensity signal S1; and
- the second intensity signal S2 and the fourth intensity signal S4 are larger than the third intensity signal S3; and
- the first intensity signal S1, the second intensity signal S2, the third intensity signal S3, the fourth intensity signal S4 and the fifth intensity signal S5 are larger than the sixth intensity signal S6.

In an embodiment of the present invention, the wavelength of the fifth wavelength light is 450 nm, and the wavelength of the sixth wavelength light is 600 nm. Therefore, in the present embodiment, the mobile device 10 further generates the fifth intensity signal S5 relating to the 450 nm wavelength and the sixth intensity signal S6 relating to the 600 nm wavelength light in the second light beam L2. The light detecting module 13 collects two more intensity signals relating to two more feature points in the target spectrum, so that the processor unit 11 has more detailed conditions to determine whether to generate a positive result information, thus improving the accuracy of the processor unit 11.

Figure 9:
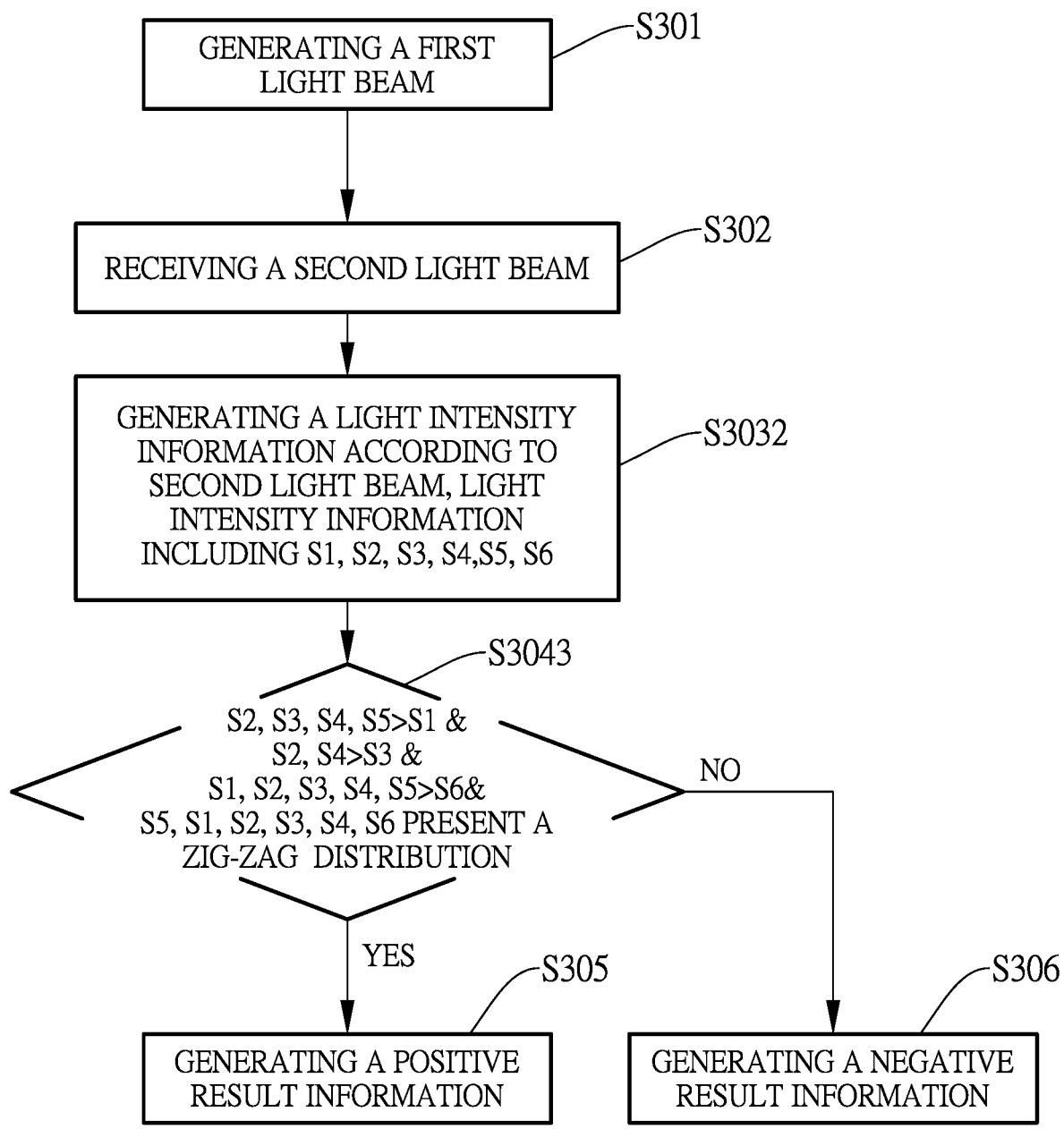
FIG. 9 is a flow chart of a third embodiment of the hemoglobin detecting method of the present invention.

With reference to FIG. 9, in a third embodiment of the present invention, when the processor unit 11 determines whether the absorption spectrum of the analyte solution matches the target spectrum, the processor further determines if the fifth intensity signal S5, the first intensity signal S1, the second intensity signal S2, the third intensity signal S3, the fourth intensity signal S4 and the sixth intensity signal S6 present a zig-zag distribution (S3043). The processor unit 11 determines the absorption spectrum of the analyte solution matches the target spectrum (S305) only if:
- the second intensity signal S2, the third intensity signal S3, the fourth intensity signal S4 and the fifth intensity signal S5 are larger than the first intensity signal S1;
- the second intensity signal S2 and the fourth intensity signal S4 are larger than the third intensity signal S3;
- the first intensity signal S1, the second intensity signal S2, the third intensity signal S3, the fourth intensity signal S4 and the fifth intensity signal S5 are larger than the sixth intensity signal S6; and
- the fifth intensity signal S5, the first intensity signal S1, the second intensity signal S2, the third intensity signal S3, the fourth intensity signal S4 and the sixth intensity signal S6 present a zig-zag distribution.

Figure 10:
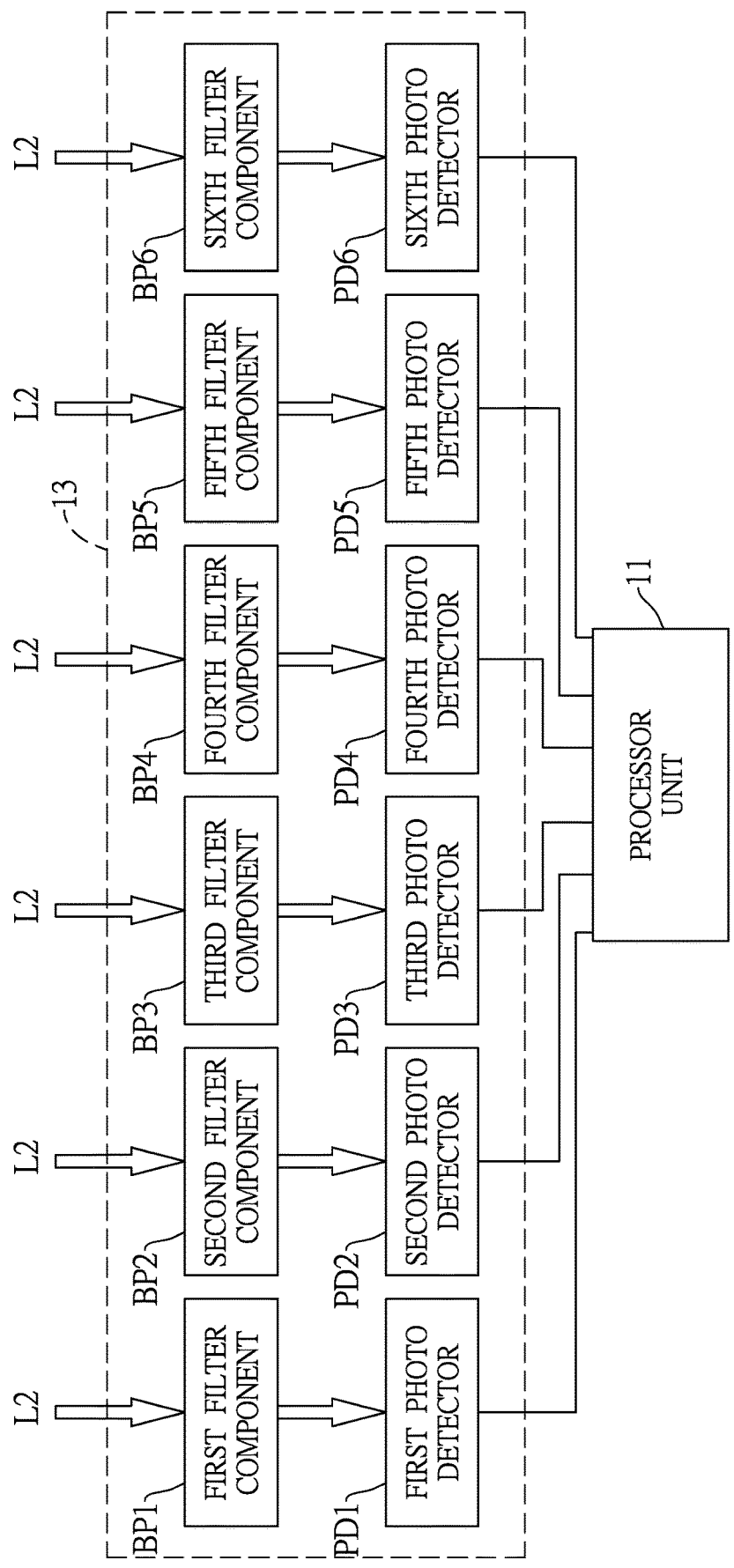
FIG. 10 is a block diagram of the light detecting module of a second embodiment of a mobile device having a hemoglobin detecting function of the present invention.

With reference to FIG. 10, in the present embodiment, in order to obtain the first to the sixth intensity signals S6, the light detecting module 13 further includes a fifth filter component, a sixth filter component, a fifth photo detector PD5, and a sixth photo detector PD6. The fifth photo detector PD5 receives the fifth wavelength light through the fifth filter component. The sixth photo detector PD6 receives the sixth wavelength light through the sixth filter component. Furthermore, the fifth filter component BP5 is a 450 nm bandpass filter, and the sixth filter component BP6 is a 600 nm bandpass filter. Therefore, the second light beam L2 is filtered to form the fifth wavelength light and the sixth wavelength light, so that the fifth photo detector PD5 and the sixth photo detector PD6 generate the fifth intensity signal S5 and the sixth intensity signal S6 respectively.

In the present embodiment, the light detecting module 13 further collects the fifth wavelength light with wavelength of 450 nm and the sixth wavelength light with wavelength of 600 nm, generating six light intensity signals in total. The two additional feature points according to the target spectrum further improve the accuracy of the test results.

In a fourth embodiment of the present invention, the mobile device 10 is a smart device, for example, a smart phone or a tablet computer. The mobile device 10 includes a shell component 15 and a display module 16. The processor unit 11 and the first light source 12 are mounted in the shell component 15. The shell component 15 has a top surface 151 and a bottom surface 152. The display module 16 is mounted on the top surface 151 of the shell component 15. When the processor unit 11 generates the positive result information, the processor unit 11 controls the display module 16 to display a positive result icon. When the processor unit 11 generates the negative result information, the processor unit 11 controls the display module 16 to display a negative result icon.

The processor unit 11 may be the main processor of the mobile device 10, while the display module 16 is the display panel of the mobile device 10, such as a touchable liquid-crystal display module 16. When the user turns on the first light module and points it to the analyte solution in the toilet bowl to perform the test and the processor unit 11 generates the result information according to light intensity information, the mobile device 10 displays a corresponding icon.

Figure 11A:
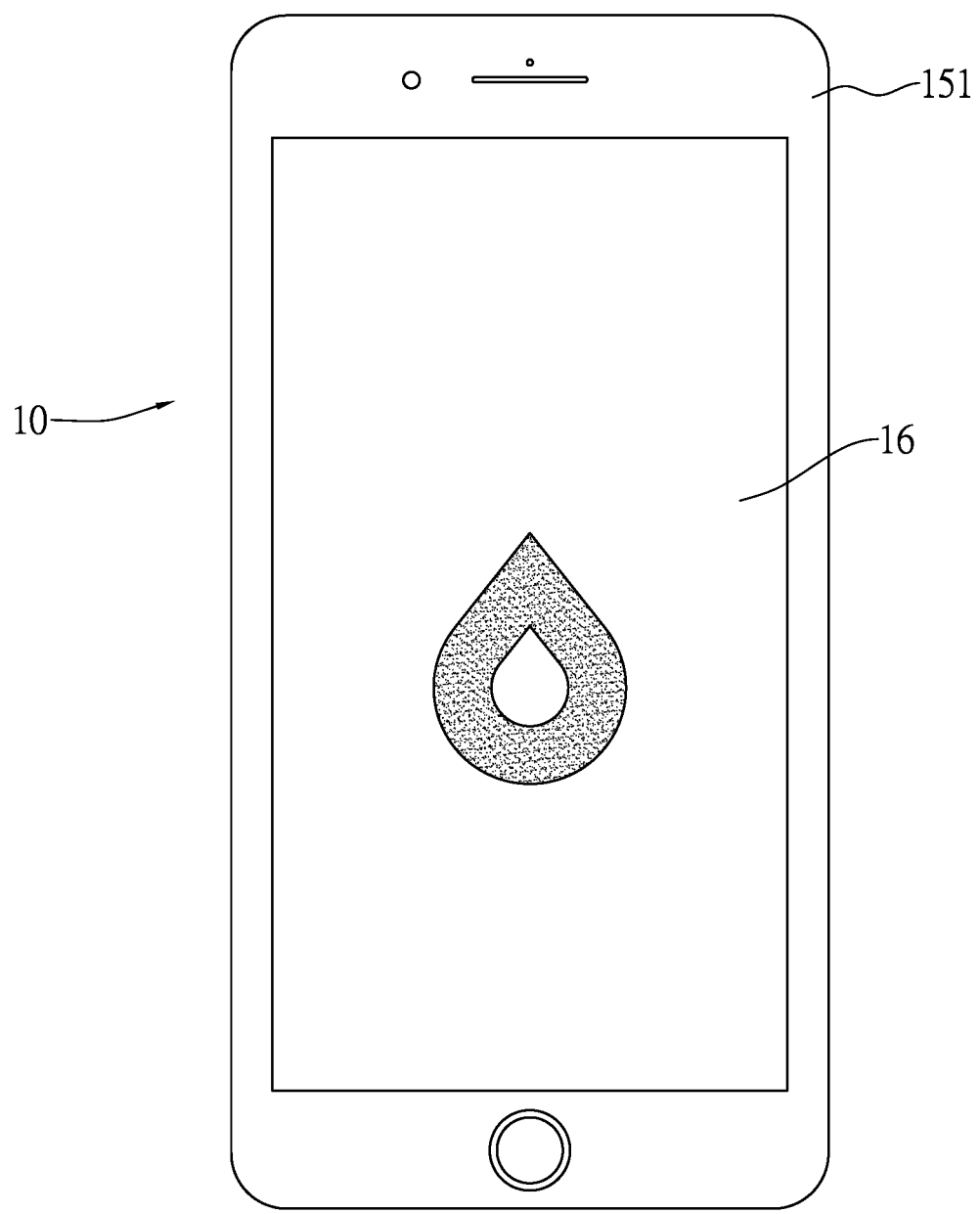
FIG. 11A and FIG. 11B are schematic views of a fourth embodiment of a mobile device having the hemoglobin detecting function of the present invention.
Figure 11B:
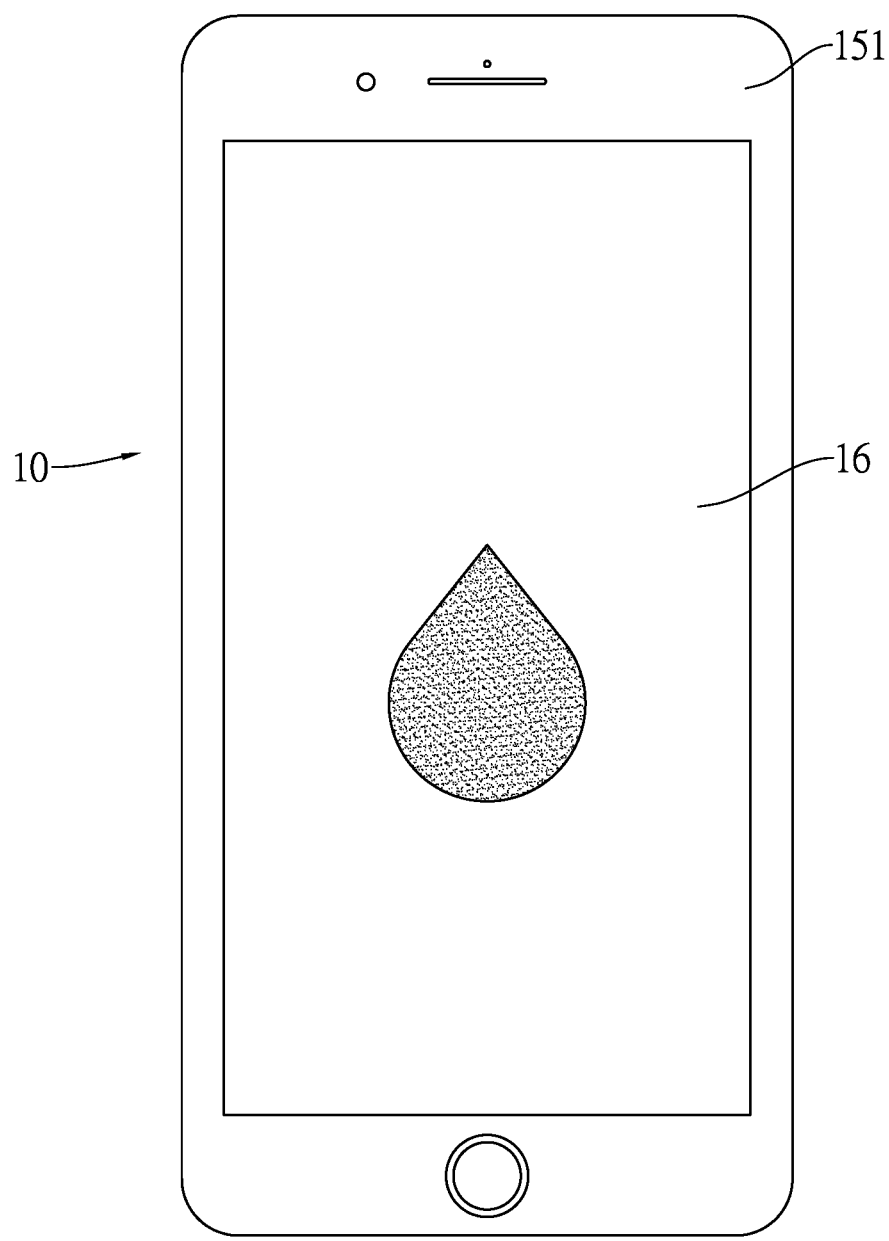

For example, with reference to FIG. 11A, when the processor unit 11 generates a negative result information, the display panel displays an icon of a hollow blood drop figure, indicating that the analyte solution does not contain any blood or hemoglobin. With reference to FIG. 11B, when the processor unit 11 generates a positive result information, the display panel displays an icon of a solid blood drop figure, indicating that the analyte solution does contain blood or hemoglobin. The result icons provide an easy and comprehensible indication of the test results for the user.

With reference to FIG. 1 and FIG. 2, in a fifth embodiment of the present invention, the mobile device 10 further includes a camera module 17 electrically connected to the processor unit 11. In the present embodiment, the light detecting module 13, the first light source 12, and the camera module 17 are mounted on the bottom surface 152 of the shell component 15. When the processor unit 11 executes an assisting program, the camera module 17 receives a target image of the analyte solution, and the processor unit 11 controls the display module 16 to display the target image, along with a suggested target position icon on the target image.

When the user points the first light beam L1 to the analyte solution in the toilet bowl, the light beam can travel through the liquid with a better transmittance if the light beam is directed to a shallow position in the container without being blocked by suspended matter in the liquid, so that the light detecting module 13 can receive a second light beam L2 with a higher intensity and obtain a more accurate test result. Furthermore, according to the shape of a toilet bowl, the better position to perform the test is a point closer to the front end of the toilet bowl, which is usually a shallower point in the toilet bowl. Therefore, when the processor unit 11 receives the target image from the camera module 17, the processor unit 11 further controls the display panel to display a suggested target position icon at the front end of the toilet bowl in the target image, providing the user with a suggested position to point the first light beam L1 thereto.

Figure 12:
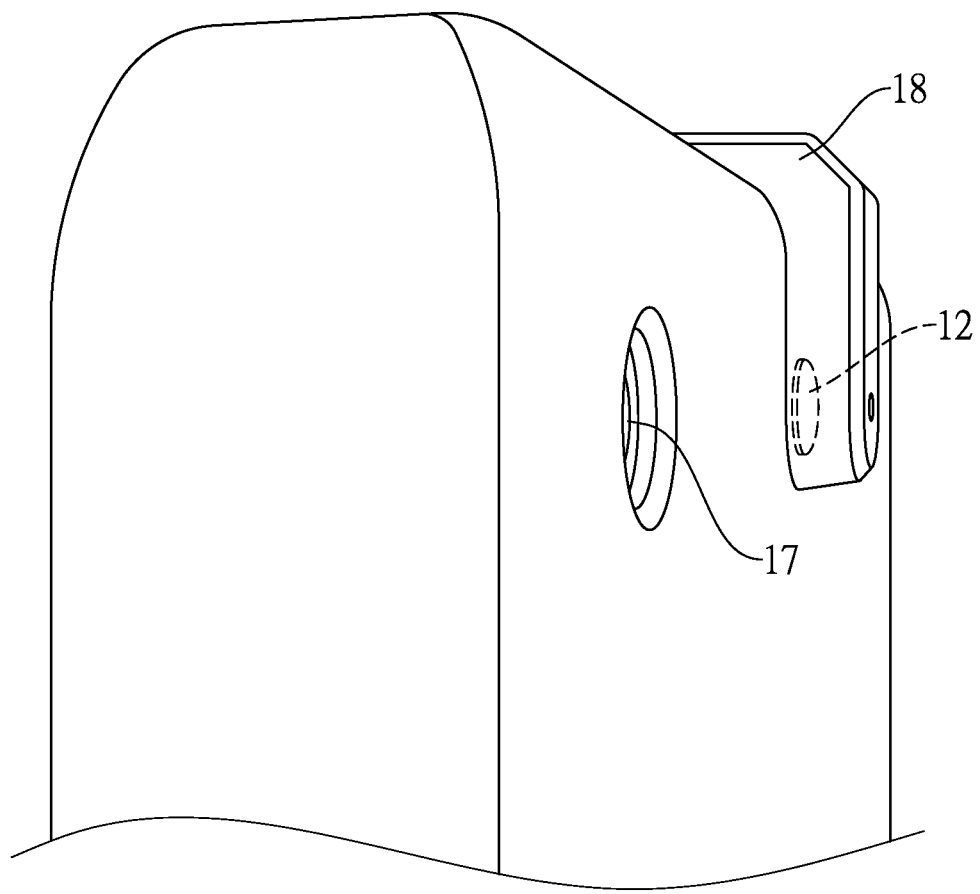
FIG. 12 is a partial perspective view of a sixth embodiment of a mobile device having a hemoglobin detecting function of the present invention.
Figure 13:
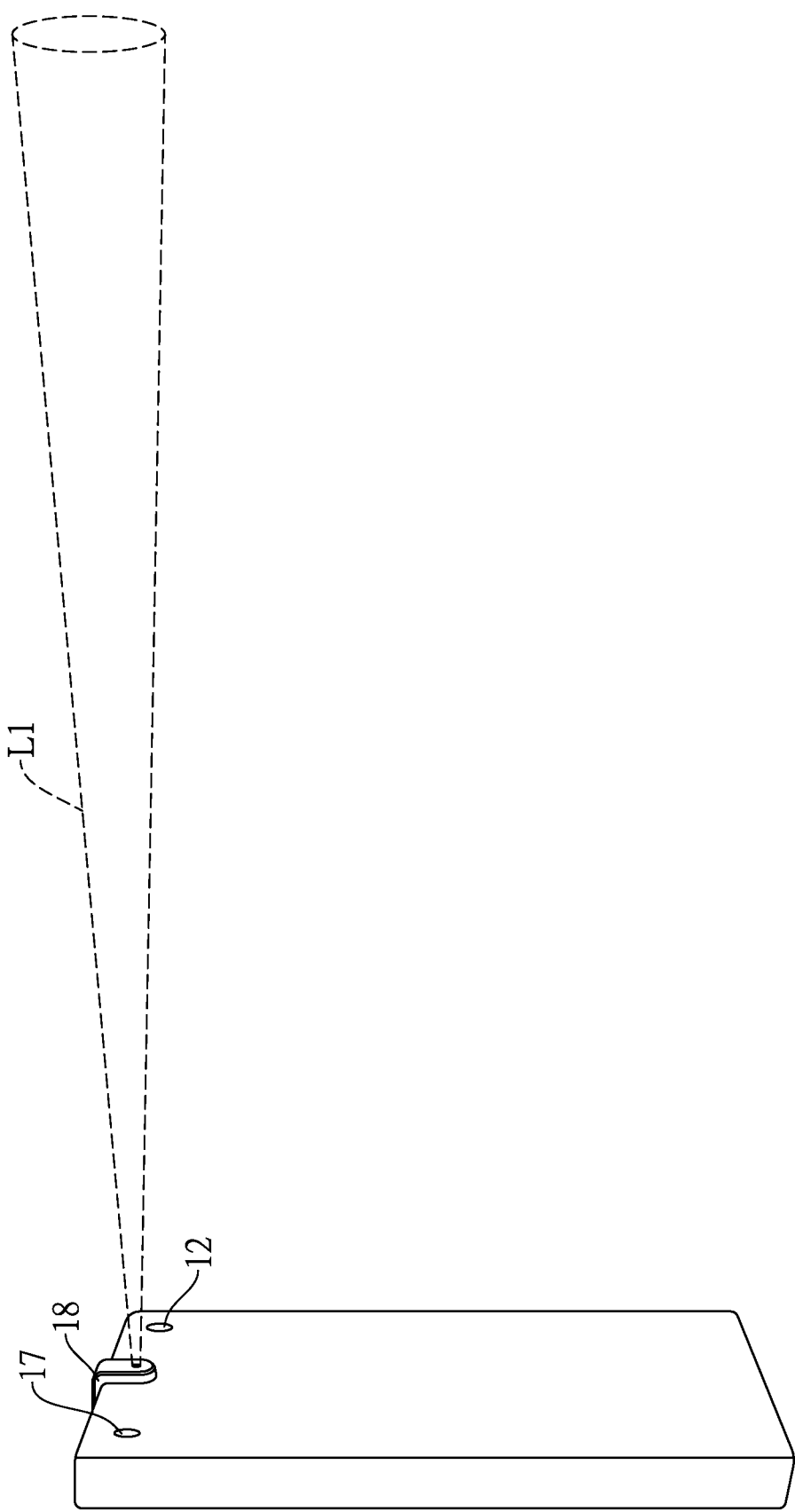
FIG. 13 is an operational view of a sixth embodiment of a mobile device having a hemoglobin detecting function of the present invention.

With reference to FIG. 12 and FIG. 13, in a sixth embodiment of the present invention, the mobile device 10 further includes a concentrator component 18. The concentrator component 18 is mounted outside the shell component 15 and clamped with the shell component 15 according to the position of the first light source 12. In the embodiment, the concentrator component is a condenser lens.

In the present embodiment, the camera module 17 is the camera lens module deployed for the smart mobile device 10, and the first light source 12 is the assistance light source or the flash light module deployed for the camera module 17. Therefore, there is no need to install an additional light source in the mobile device 10 for hemoglobin detection.

Furthermore, since the first light source 12 is the assistance light source or the flash light module for the regular camera module 17 and the first light source 12 is settled for illumination, the first light beam L1 usually has a wide divergence angle and a low illuminating intensity per area unit. Therefore, the concentration component 18 concentrates the first light beam L1 and forms a more condensed first light beam L1 with higher intensity per unit area. When the concentrated first light beam L1 incidentally travels through the analyte solution and is reflected by the inside surface of the toilet bowl, it forms a second light beam L2 with a better intensity, improving the accuracy of the test. The concentration component 18 is removable, so that the user can remove the concentration component 18 when not performing the hemoglobin detection, and use the first light source 12 as a normal assistance light source.

Figure 14:
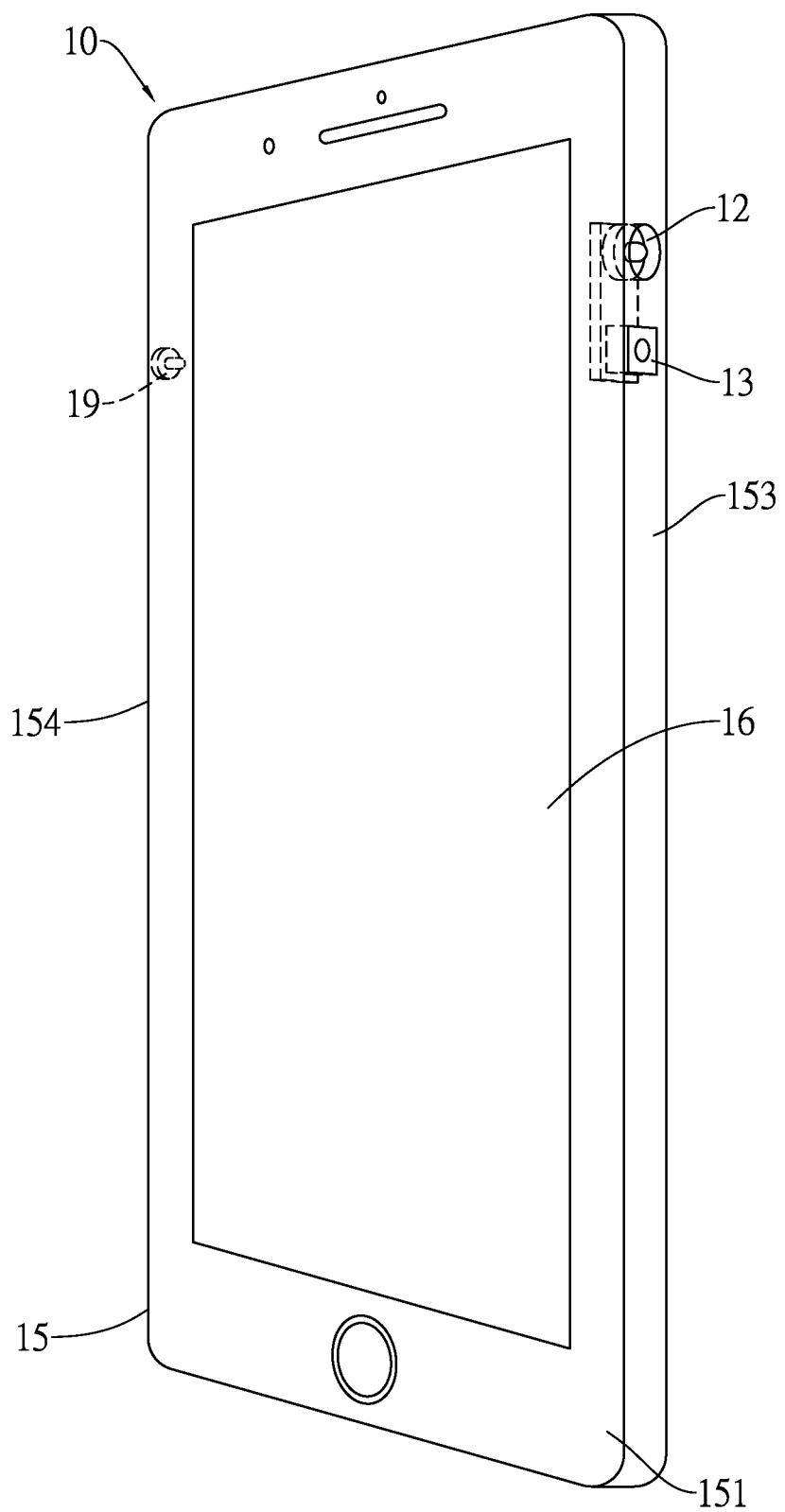
FIG. 14 is a perspective view of a seventh embodiment of a mobile device having a hemoglobin detecting function of the present invention.
Figure 15:
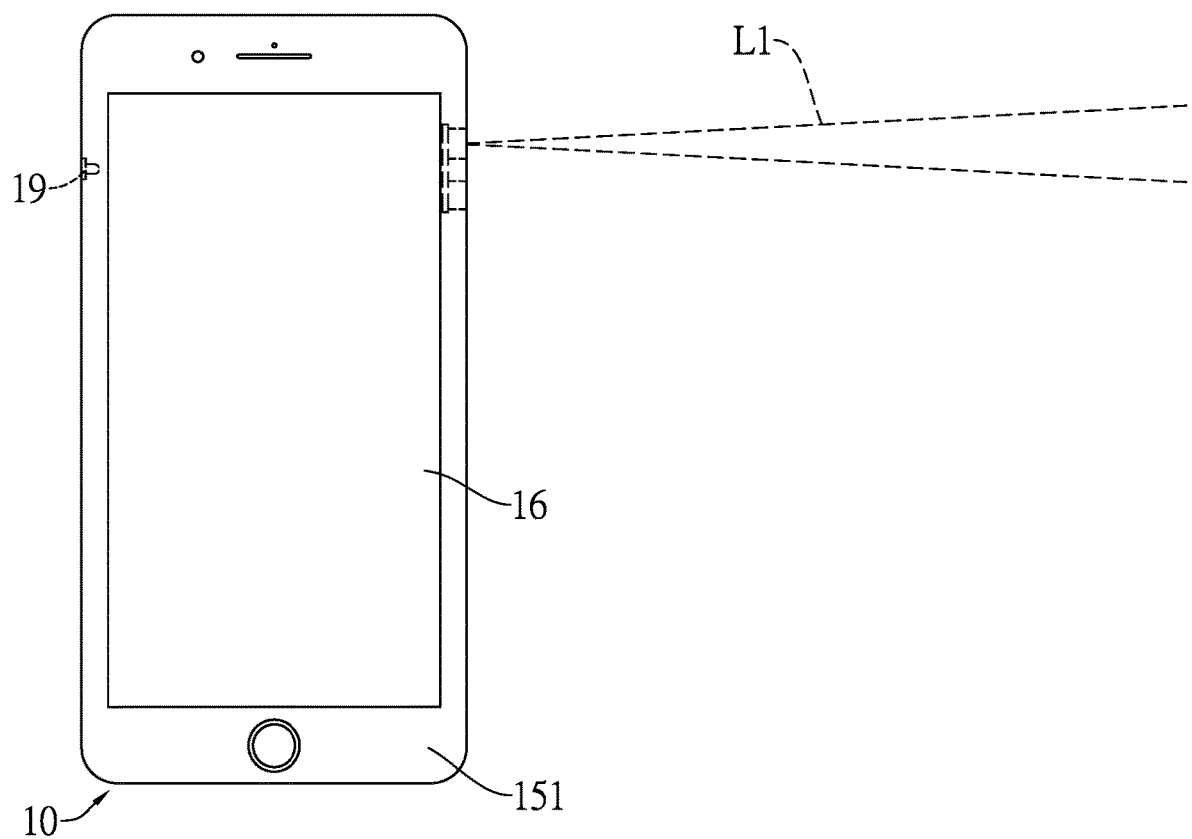
FIG. 15 is an operational view of a seventh embodiment of a mobile device having a hemoglobin detecting function of the present invention.

With reference to FIG. 14 and FIG. 15, in a seventh embodiment of the present invention, the shell component 15 has a first side surface 153 and a second side surface 154. The two opposite edges of the first side surface 153 and the two opposite edges of the second side surface 154 are connected to the top surface 151 and the bottom surface 152 respectively. In the present embodiment, the first light source 12 and the light detecting module 13 are mounted on the first side surface 153 of the shell component 15.

Furthermore, the mobile device 10 further includes a controlling button 19, which is electrically connected to the processor unit 11 and mounted in the second side surface 154 of the shell component 15. When the controlling button 19 is switched to an on-state, the first light source 12 generates the first light beam L1, and the light detecting module 13 receives the second light beam L2 and generates the light intensity information.

The present embodiment is another design for the arrangement of the first light source 12 and the light detecting module 13, deploying the first light source 12 and the light detecting module 13 on the first side surface 153, which also allows the user to hold the mobile device 10 easily and point the first light source 12 and the light detecting module 13 to the target. The first light source 12 in the present embodiment is installed especially for the hemoglobin detecting function, not providing assistance illumination function for photographing function. Therefore the first light source 12 may provide the first light beam L1 with a narrow divergence angle and a high illuminating intensity per area unit, which is a concentrated light beam that results in high accuracy of the hemoglobin detection without the aid of an additional concentration component 18.

Even though numerous characteristics and advantages of the present invention have been set forth in the foregoing description, together with details of the structure and function of the invention, the disclosure is illustrative only. Changes may be made in detail, especially in matters of shape, size, and arrangement of parts within the principles of the invention to the full extent indicated by the broad general meaning of the terms in which the appended claims are expressed.

What is claimed is:

1. A mobile device having a hemoglobin detecting function, wherein the mobile device is a smart phone, comprising:
   a processor unit;
   a first light source, generating a first light beam;
   a light detecting module, electrically connected to the processor unit; wherein the light detecting module receives a second light beam and generates a light intensity information according to the second light beam; wherein
   the first light beam passes through an analyte solution and is reflected to form the second light beam; the second light beam includes a first wavelength light, a second wavelength light, a third wavelength light, and a fourth wavelength light, wherein a wavelength of the first wavelength light is smaller than a wavelength of the second wavelength light, the wavelength of the second wavelength light is smaller than a wavelength of the third wavelength light, and the wavelength of the third wavelength light is smaller than a wavelength of the fourth wavelength light;
   the light intensity information includes a first intensity signal relating to the first wavelength light, a second intensity signal relating to the second wavelength light, a third intensity signal relating to the third wavelength light, and a fourth intensity signal relating to the fourth wavelength light;
   the processor unit receives the light intensity information from the light detecting module, and determines whether an absorption spectrum of the analyte solution matches a target spectrum; wherein the absorption spectrum of the analyte solution matches the target spectrum if:
     the second intensity signal, the third intensity signal and the fourth intensity signal are larger than the first intensity signal; and
     the second intensity signal and the fourth intensity signal are larger than the third intensity signal;
   when the absorption spectrum of the analyte solution matches the target spectrum, the processor unit generates a positive result information, indicating that the analyte solution contains hemoglobin;
   when the absorption spectrum of the analyte solution does not match the target spectrum, the processor unit generates a negative result information, indicating that the analyte solution does not contain hemoglobin.

2. The mobile device having the hemoglobin detecting function as claimed in claim 1, wherein the processor unit further determines whether the first intensity signal, the second intensity signal, the third intensity signal, and the fourth intensity signal present a zig-zag distribution;
   wherein the absorption spectrum of the analyte solution matches the target spectrum if:
      the second intensity signal, the third intensity signal, and the fourth intensity signal are larger than the first intensity signal;
      the second intensity signal and the fourth intensity signal are larger than the third intensity signal; and
      the first intensity signal, the second intensity signal, the third intensity signal and the fourth intensity signal present a zig-zag distribution.

3. The mobile device having the hemoglobin detecting function as claimed in claim 1, wherein the wavelength of the first wavelength light is 500 nm, the wavelength of the second wavelength light is 541 nm, the wavelength of the third wavelength light is 550 nm, and the wavelength of the fourth wavelength light is 577 nm.

4. The mobile device having the hemoglobin detecting function as claimed in claim 1, wherein the light intensity information further includes a fifth intensity signal relating to a fifth wavelength light, and a sixth intensity signal relating to a sixth wavelength light; wherein a wavelength of the fifth wavelength light is smaller than the wavelength of the first wavelength light, and a wavelength of the sixth wavelength light is larger than the wavelength of the fourth wavelength light;
   wherein the processor unit further determines whether the fifth intensity signal is larger than the first intensity signal, and whether the fifth intensity signal, the first intensity signal, the second intensity signal, the third intensity signal, and the fourth intensity signal are larger than the sixth intensity signal;
   wherein the absorption spectrum of the analyte solution matches the target spectrum if:
      the fifth intensity signal, the second intensity signal, the third intensity signal, and the fourth intensity signal are larger than the first intensity signal
      the second intensity signal and the fourth intensity signal are larger than the third intensity signal; and
      the fifth intensity signal, the first intensity signal, the second intensity signal, the third intensity signal, and the fourth intensity signal are larger than the sixth intensity signal.

5. The mobile device having the hemoglobin detecting function as claimed in claim 4, wherein the processor unit further determines whether the fifth intensity signal, the first intensity signal, the second intensity signal, the third intensity signal, the fourth intensity signal, and the sixth intensity signal present a zig-zag distribution;
   wherein the absorption spectrum of the analyte solution matches the target spectrum if:
      the fifth intensity signal, the second intensity signal, the third intensity signal, and the fourth intensity signal are larger than the first intensity signal
      the second intensity signal and the fourth intensity signal are larger than the third intensity signal;
      the fifth intensity signal, the first intensity signal, the second intensity signal, the third intensity signal, and the fourth intensity signal are larger than the sixth intensity signal; and
      the fifth intensity signal, the first intensity signal, the second intensity signal, the third intensity signal, the fourth intensity signal, and the sixth intensity signal present a zig-zag distribution.

6. The mobile device having the hemoglobin detecting function as claimed in claim 4, wherein the wavelength of the fifth wavelength light is 450 nm, and the wavelength of the sixth wavelength light is 600 nm.

7. The mobile device having the hemoglobin detecting function as claimed in claim 4, wherein the light detecting module comprises:
   a first filter component;
   a first photo detector, receiving the first wavelength light through the first filter component, and generating the first intensity signal according to the first wavelength light;
   a second filter component;
   a second photo detector, receiving the second wavelength light through the second filter component, and generating the second intensity signal according to the second wavelength light;
   a third filter component;
   a third photo detector, receiving the third wavelength light through the third filter component, and generating the third intensity signal according to the third wavelength light;
   a fourth filter component;
   a fourth photo detector, receiving the fourth wavelength light through the fourth filter component, and generating the fourth intensity signal according to the fourth wavelength light;
   a fifth filter component;
   a fifth photo detector, receiving the fifth wavelength light through the fifth filter component, and generating the fifth intensity signal according to the fifth wavelength light;
   a sixth filter component;
   a sixth photo detector, receiving the sixth wavelength light through the sixth filter component, and generating the sixth intensity signal according to the sixth wavelength light.

8. The mobile device having the hemoglobin detecting function as claimed in claim 1, wherein the light detecting module comprises:
   a first filter component;
   a first photo detector, receiving the first wavelength light through the first filter component, and generating the first intensity signal according to the first wavelength light;
   a second filter component;
   a second photo detector, receiving the second wavelength light through the second filter component, and generating the second intensity signal according to the second wavelength light;
   a third filter component;
   a third photo detector, receiving the third wavelength light through the third filter component, and generating the third intensity signal according to the third wavelength light;
   a fourth filter component;
   a fourth photo detector, receiving the fourth wavelength light through the fourth filter component, and generating the fourth intensity signal according to the fourth wavelength light.

9. The mobile device having the hemoglobin detecting function as claimed in claim 1, wherein
   the mobile device is a smart mobile device, further comprising a shell component and a display module, and the processor unit and the first light source are mounted in the shell component;

the shell component has a top surface and a bottom surface, and the display module is mounted on the top surface of the shell component;

when the processor unit generates the positive result information, the processor unit controls the display module to display a positive result icon; and when the processor unit generates the negative result information, the processor unit controls the display module to display a negative result icon.

10. The mobile device having the hemoglobin detecting function as claimed in claim 9, further comprising:

a camera module, electrically connected to the processor unit, wherein the camera module, the first light source and the light detecting module are mounted on the bottom surface of the shell component; wherein when the processor unit executes an assisting program, the camera module receives a target image of the analyte solution, and the processor unit controls the display module to display the target image, and a suggested target position icon.

11. The mobile device having the hemoglobin detecting function as claimed in claim 10, further comprising:

a concentrator component, disposed on the shell component and engaged with the shell component, wherein the concentrator component is disposed according to a position of the first light source.

12. The mobile device having the hemoglobin detecting function as claimed in claim 9, wherein the shell component has a first side surface and a second side surface, two opposite edges of the first side surface and two opposite edges of the second side surface are respectively connected to the top surface and the bottom surface;

wherein the first light source and the light detecting module are mounted in the first side surface of the shell component.

13. The mobile device having the hemoglobin detecting function as claimed in claim 12, further comprising:

a controlling button, electrically connected to the processor unit, and mounted in the second side surface of the shell component;

wherein when the controlling button is switched on, the first light source generates the first light beam, and the light detecting module receives the second light beam.

14. A hemoglobin detecting method, executed by a mobile device, wherein the mobile device is a smart phone, comprising the following steps:

generating a first light beam;

receiving a second light beam; wherein the first light beam passes through an analyte solution and is reflected to form the second light beam; wherein the second light beam includes a first wavelength light, a second wavelength light, a third wavelength light, and a fourth wavelength light;

generating a light intensity information according to the second light beam; wherein the light intensity information includes a first intensity signal relating to the first wavelength light, a second intensity signal relating to the second wavelength light, a third intensity signal relating to the third wavelength light, and a fourth intensity signal relating to the fourth wavelength light;

determining whether an absorption spectrum of the analyte solution matches a target spectrum according to the light intensity information; wherein the absorption spectrum of the analyte solution matches the target spectrum if:

the second intensity signal, the third intensity signal and the fourth intensity signal are larger than the first intensity signal; and the second intensity signal and the fourth intensity signal are larger than the third intensity signal;

when the absorption spectrum of the analyte solution matches the target spectrum, generating a positive result information, indicating that the analyte solution contains hemoglobin;

when the absorption spectrum of the analyte solution does not match the target spectrum, generating a negative result information, indicating that the analyte solution does not contain hemoglobin.

15. The hemoglobin detecting method as claimed in claim 14, wherein the step of determining whether the absorption spectrum of the analyte solution matches a target spectrum further includes the following steps:

determining whether the first intensity signal, the second intensity signal, the third intensity signal, and the fourth intensity signal present a zig-zag distribution; wherein the absorption spectrum of the analyte solution matches the target spectrum if:

the second intensity signal, the third intensity signal and the fourth intensity signal are larger than the first intensity signal;

the second intensity signal and the fourth intensity signal are larger than the third intensity signal; and the first intensity signal, the second intensity signal, the third intensity signal and the fourth intensity signal present a zig-zag distribution.

16. The hemoglobin detecting method, as claimed in claim 14, wherein a wavelength of the first wavelength light is 500 nm, a wavelength of the second wavelength light is 541 nm, a wavelength of the third wavelength light is 550 nm, and a wavelength of the fourth wavelength light is 577 nm.

17. The hemoglobin detecting method as claimed in claim 16, wherein the light intensity information further includes a fifth intensity signal relating to a fifth wavelength light, and a sixth intensity signal relating to a sixth wavelength light; wherein the wavelength of the fifth wavelength light is smaller than the wavelength of the first wavelength light, and the wavelength of the sixth wavelength light is larger than the wavelength of the fourth wavelength light;

the step of determining whether the absorption spectrum of the analyte solution matches a target spectrum further includes the following steps:

determining whether the fifth intensity signal is larger than the first intensity signal, and determining whether the fifth intensity signal, the first intensity signal, the second intensity signal, the third intensity signal, and the fourth intensity signal are larger than the sixth intensity signal; wherein the absorption spectrum of the analyte solution matches the target spectrum if:

the fifth intensity signal, the second intensity signal, the third intensity signal, and the fourth intensity are larger than the first intensity signal;

the second intensity signal and the fourth intensity signal are larger than the third intensity signal; and the fifth intensity signal, the first intensity signal, the second intensity signal, the third intensity signal, and the fourth intensity signal are larger than the sixth intensity signal.

18. The hemoglobin detecting method as claimed in claim 17, wherein the step of determining whether the absorption spectrum of the analyte solution matches a target spectrum further includes the following steps:

determining whether the fifth intensity signal, the first intensity signal, the second intensity signal, the third intensity signal, the fourth intensity signal, and the sixth intensity signal present a zig-zag distribution; wherein the absorption spectrum of the analyte solution matches the target spectrum if:

the fifth intensity signal, the second intensity signal, the third intensity signal, and the fourth intensity signal are larger than the first intensity signal;

the second intensity signal and the fourth intensity signal are larger than the third intensity signal; and the fifth intensity signal, the first intensity signal, the second intensity signal, the third intensity signal, and the fourth intensity signal are larger than the sixth intensity signal; and the fifth intensity signal, the first intensity signal, the second intensity signal, the third intensity signal, the fourth intensity signal, and the sixth intensity signal present a zig-zag distribution.

19. The hemoglobin detecting method as claimed in claim 18, wherein a wavelength of the fifth wavelength light is 450 nm, and a wavelength of the sixth wavelength light is 600 nm.

* * * * *